(12) United States Patent
Baltzer

(10) Patent No.: US 7,230,072 B2
(45) Date of Patent: Jun. 12, 2007

(54) SITE-SELECTIVE ACYL TRANSFER

(75) Inventor: Lars Baltzer, Göteborg (SE)

(73) Assignee: Modpro AB, Göteborg (SE)

( * ) Notice: Subject to any disclaimer, the term of this patent is extended or adjusted under 35 U.S.C. 154(b) by 380 days.

(21) Appl. No.: 10/258,445

(22) PCT Filed: May 7, 2001

(86) PCT No.: PCT/SE01/00987

§ 371 (c)(1),
(2), (4) Date: Oct. 24, 2002

(87) PCT Pub. No.: WO01/85756

PCT Pub. Date: Nov. 15, 2001

(65) Prior Publication Data

US 2004/0161815 A1 Aug. 19, 2004

(51) Int. Cl.
*C07K 1/02* (2006.01)
(52) U.S. Cl. ................................ 530/300; 530/350
(58) Field of Classification Search ............... None
See application file for complete search history.

(56) References Cited

U.S. PATENT DOCUMENTS 6,171,819 B1 * 1/2001 Ahlberg et al. ............ 435/69.1

FOREIGN PATENT DOCUMENTS

| WO | WO 97/43302 | 11/1997 |
|----|-------------|---------|
| WO | WO 98/55501 | 12/1998 |
| WO | WO 00/32623 | 6/2000  |

OTHER PUBLICATIONS

Biochemistry 1987, "Site-Directed Mutagenesis Reveals Transition-State Stabilization" Thor J. Borgford, Abstract, p. 7247 col. 2 line 23—p. 7249 col. 2 line 27.
J. Am. Chem. Soc. 1998, "Cooperative Neucleophilic and General-Acid Catalysis", Kerstin S. Broo, Abstract, p. 4063 col. 2 line 5-15, p. 4064 col. 2 line 32—p. 4067 col. 2 line 14.
Biochemistry 1996, "Conversion of Serine-114 to Cysteine-114 and the Role of the Active Site Nucleophile in Acyl Transfer by Myristol-ACP Thioesterase from *Vibrio harveyi* +", Jun Li, Abstract, p. 9968 col. 1 line 25-35, p. 9971 col. 1 line 32—p. 9972 col. 2 line 15.

* cited by examiner

*Primary Examiner*—Nashaat T. Nashed
(74) *Attorney, Agent, or Firm*—Buchanan Ingersoll & Rooney PC

(57) ABSTRACT

A method for site-selective acyl transfer in amidation of folded polypeptides and proteins based on the use of a chemical structure element comprising an imidazole function, such as histidine, in position i flanked by at least one functional group to be amidated, such as lysinc, in position i+3+4k. where K is an integer equal to or higher than −1, or in position i−4−4n, wherein n is an integer equal to or higher than 0, and at least one activating group, such as serine, in position i+4+4n or i−3−4n, respectively.

2 Claims, 1 Drawing Sheet

SEQUENCE LISTING

<160> NUMBER OF SEQ ID NOS: 11

<210> SEQ ID NO 1
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
<222> LOCATION: 8, 14, 15, 18, 19, 33, 34
<223> OTHER INFORMATION: Xaa = Any Amino Acid
<220> FEATURE:
<221> NAME/KEY: VARIANT
<222> LOCATION: 5, 8, 14, 15, 16, 18, 19, 27, 33, 34
<223> OTHER INFORMATION: Xaa = Any Amino Acid

<400> SEQUENCE: 1

Asn Ala Ala Asp Xaa Glu Ala Xaa Ile Lys His Leu Ala Xaa Xaa
 1               5                  10                  15

Ala Xaa Xaa Gly Pro Val Asp Ala Ala Gln Xaa Ala Glu Gln Leu Ala
            20                  25                  30

Xaa Xaa Phe Glu Ala Phe Ala Arg Ala Gly
        35                  40

<210> SEQ ID NO 2
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: MOD_RES
<222> LOCATION: 34
<223> OTHER INFORMATION: Orn
<220> FEATURE:
<221> NAME/KEY: VARIANT
<222> LOCATION: 5, 16, 27, 34
<223> OTHER INFORMATION: Xaa = Any Amino Acid

<400> SEQUENCE: 2

Asn Ala Ala Asp Xaa Glu Ala Ala Ile Lys His Leu Ala Glu Ser Xaa
 1               5                  10                  15

Ala Ala Lys Gly Pro Val Asp Ala Ala Gln Xaa Ala Glu Gln Leu Ala
            20                  25                  30

-continued

```
Lys Xaa Phe Glu Ala Phe Ala Arg Ala Gly
        35                  40

<210> SEQ ID NO 3
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: MOD_RES
<222> LOCATION: 34
<223> OTHER INFORMATION: Orn
<220> FEATURE:
<221> NAME/KEY: VARIANT
<222> LOCATION: 5, 16, 27, 34
<223> OTHER INFORMATION: Xaa = Any Amino Acid

<400> SEQUENCE: 3

Asn Ala Ala Asp Xaa Glu Ala Ser Ile Lys His Leu Ala Glu Ala Xaa
1               5                   10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 4
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: MOD_RES
<222> LOCATION: 34
<223> OTHER INFORMATION: Orn
<220> FEATURE:
<221> NAME/KEY: VARIANT
<222> LOCATION: 5, 16, 27, 34
<223> OTHER INFORMATION: Xaa = Any Amino Acid

<400> SEQUENCE: 4

Asn Ala Ala Asp Xaa Glu Ala Ala Ile Lys His Leu Ala Lys Ser Xaa
1               5                   10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
```

<210> SEQ ID NO 5
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
<222> LOCATION: 5, 16, 27
<223> OTHER INFORMATION: Xaa = Any Amino Acid

<400> SEQUENCE: 5

Asn Ala Ala Asp Xaa Glu Ala Ala Ile Lys His Leu Ala Lys Ser Xaa
 1               5                  10                  15

Ala Ala Lys Gly Pro Val Asp Ala Ala Gln Xaa Ala Glu Gln Leu Ala
            20                  25                  30

Lys Ala Phe Glu Ala Phe Ala Arg Ala Gly
        35                  40

<210> SEQ ID NO 6
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
<222> LOCATION: 5, 16, 27
<223> OTHER INFORMATION: Xaa = Any Amino Acid

<400> SEQUENCE: 6

Asn Ala Ala Asp Xaa Glu Ala Ala Ile Lys His Leu Ala Lys Ala Xaa
 1               5                  10                  15

Ala Ala Lys Gly Pro Val Asp Ala Ala Gln Xaa Ala Glu Gln Leu Ala
            20                  25                  30

Lys Ala Phe Glu Ala Phe Ala Arg Ala Gly
        35                  40

<210> SEQ ID NO 7
<211> LENGTH: 42
<212> TYPE: PRT
<213> ORGANISM: Artificial Sequence
<220> FEATURE:
<223> OTHER INFORMATION: Peptide of natural or synthetic origin

```
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: MOD_RES
<222> LOCATION: 34
<223> OTHER INFORMATION: Orn
<220> FEATURE:
<221> NAME/KEY: VARIANT
<222> LOCATION: 5, 16, 27, 34
<223> OTHER INFORMATION: Xaa = Any Amino Acid

<400> SEQUENCE: 7

Asn Ala Ala Asp Xaa Glu Ala Ser Ile Lys His Leu Ala Lys Ala Xaa
 1               5                  10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
        35                  40

<210> SEQ ID NO 8
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
<222> LOCATION: 5, 16, 27
<223> OTHER INFORMATION: Xaa = Any Amino Acid

<400> SEQUENCE: 8

Asn Ala Ala Asp Xaa Glu Ala Ala Ile Lys His Leu Ala Glu Ser Xaa
 1               5                  10                  15

Ala Lys Ser Gly Pro Val Asp Ala Ala Gln Xaa Ala Glu Gln Leu Ala
            20                  25                  30

Lys Ala Phe Glu Ala Phe Ala Arg Ala Gly
        35                  40

<210> SEQ ID NO 9
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
```

```
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
<222> LOCATION: 5, 16, 27
<223> OTHER INFORMATION: Xaa = Any Amino Acid

<400> SEQUENCE: 9

Asn Ala Ala Asp Xaa Glu Ala Ala Ile Lys His Leu Ala Glu Ser Xaa
 1               5                  10                  15

Ala Lys Ala Gly Pro Val Asp Ala Ala Gln Xaa Ala Glu Gln Leu Ala
            20                  25                  30

Lys Ala Phe Glu Ala Phe Ala Arg Ala Gly
            35                  40

<210> SEQ ID NO 10
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
<222> LOCATION: 5, 16, 27
<223> OTHER INFORMATION: Xaa = Any Amino Acid

<400> SEQUENCE: 10

Asn Ala Ala Asp Xaa Glu Ala Ala Ile Lys His Leu Ala Glu Ala Xaa
 1               5                  10                  15

Ala Ala Lys Gly Pro Val Asp Ala Ala Gln Xaa Ala Glu Gln Leu Ala
            20                  25                  30

Lys Ser Phe Glu Ala Phe Ala Arg Ala Gly
            35                  40

<210> SEQ ID NO 11
<211> LENGTH: 42
<212> TYPE: PRT
<213> ORGANISM: Artificial Sequence
<220> FEATURE:
<223> OTHER INFORMATION: Peptide of natural or synthetic origin
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 42
<223> OTHER INFORMATION: AMIDATION
<220> FEATURE:
<221> NAME/KEY: MOD_RES
<222> LOCATION: 5,16,27
<223> OTHER INFORMATION: Nle
<220> FEATURE:
<221> NAME/KEY: VARIANT
```

```
<222> LOCATION: 5, 16, 27
<223> OTHER INFORMATION: Xaa = Any Amino Acid

<400> SEQUENCE: 11

Asn Ala Ala Asp Xaa Glu Ala Ser Ile Lys His Leu Ala Glu Ala Xaa
 1               5                  10                  15

Ala Ala Lys Gly Pro Val Asp Ala Ala Gln Xaa Ala Glu Gln Leu Ala
            20                  25                  30

Lys Ala Phe Glu Ala Phe Ala Arg Ala Gly
            35                  40
```

SITE-SELECTIVE ACYL TRANSFER

FIELD OF THE INVENTION

The present invention relates to site-selective acyl transfer.

BACKGROUND OF THE INVENTION

So-called acyl transfer reactions involve the transfer of an acyl group (the residue of an organic acid after removal of the carboxyl hydroxy group) either internally within a chemical species or from one chemical species to another. Examples are amide formation, transesterification and hydrolysis.

It is well known that acyl transfer reactions can be catalyzed by imidazole in aqueous solution, the imidazole, which is a strong nucleophile, forming an intermediary reactive complex with the acyl group. Also polymer-supported imidazoles have been used as acyl transfer catalysts (see e.g. Skjujins, A., et al., Latv. PSR Zinat. Akad. Vestis, Kim. Ser. 1988 (6), 720–5).

It has further been shown that small peptides containing a histidine (His) residue (an amino acid which contains an imidazolyl group) can have hydrolytic activity.

Recent progress in designing structural proteins and peptides has resulted in the preparation of several peptides with substantial catalytic activity (W. F. DeGrado, Nature, 365, 488 (1993). For example, K. Johnsson et al., Nature, 365, 530 (1993) disclose a short self-associating Leu-Lys-rich helical peptide that accelerates the rate of decarboxylation by means of a Schiff's base intermediate between a substrate of oxaloacetate and an amine with an electrostatically depressed acid constant ($K_a$). It is mentioned that the secondary structure is important for the activity.

Nature's enzymes form powerful catalysts by combining residues that are by themselves only modestly reactive. It is therefore not surprising to find that sites other than those responsible for catalysis also show chemical reactivity and that unexpected reactions can occur on the protein surface. The combination of His with Lys, for example, in a helix forms a simple two-residue site where the Lys activates the His residue in its reactions with active esters and the His activates the Lys[1,2]. The overall amidation rate of the lysine is at least three orders of magnitude larger than that in the direct reaction between the lysine and the esters[1].

SUMMARY OF THE INVENTION

It has now been found that the above mentioned amidation reaction is considerably more complex and has much wider implications than first expected since the acyl groups of esters that react with His residues on the surface of proteins can migrate as covalent intermediates from the initial reaction site to form amides at the side chains of lysine residues more than 10 Å away. They undergo a series of transacylation reactions on the protein surface and, as a result, migrate from histidines to serines, from serines to serines, and from serines to lysines in pathways that appear to be strictly regulated. In fact, the situation can be compared to a complex traffic regulation system as the pathways allowed for acylgroup transfer appears to follow rules of high specificity and directionality. The implications of these acylation reactions in native proteins are that the acyl groups of esters and amides, and perhaps also the corresponding ones of phosphoesters, can be generated at sites different from the ones where the product is eventually formed. The implications for the chemistry of proteins is that post-synthetic modifications on a high level of complexity are possible using folded proteins that do not need to be protected.

The invention thus relates to the method for site-selective acyl transfer in or amidation of folded polypeptides and proteins based on the use of a chemical structure element (e.g., a polypeptide or protein comprising a helical secondary structure) comprising an imidazole function in position i flanked by at least one functional group to be amidated in position i+3+4k, where k is an integer equal to or higher than −1 or in position i−4−4n, wherein n is an integer equal to or higher than 0, characterized in that it also comprises at least one activating group in position i+4+4n or i−3−4n, respectively, wherein in is as above.

The reaction between a His residue and an ester is a two-step reaction where the first and rate-limiting step is the formation of an acyl intermediate under the release of the leaving group. In the second step the acyl intermediate reacts with the most potent nucleophile available to it. In the reaction between p-nitrophenyl esters and imidazole in aqueous solution, a model reaction for the His catalyzed one, the reaction product is the carboxylic acid and the reaction is hydrolysis. In the presence of 10 vol % trifluoroethanol the reaction product is the corresponding trifluoroethyl ester[4]. In folded proteins the intramolecularity of flanking lysine residues make them the most potent nucleophiles even at pH 5, where they are predominantly protonated and the reaction is an amide at the side chain of the lysine residue[1,2]. The rules for the His-Lys pair were reported previously[5] and a His in position i is able to acylate a Lys in position i+4 or i−3 but not in position i−3, i−4 or i−1. In order to investigate whether lysines be acylated that were more distant, proteins were designed in which amino acid residues were introduced in between His and Lys residues to mediate acyl transfers.

According to the present invention it is possible to site-selectively form amide bonds between lysine side chains and acyl groups of active esters. Anything that can be transformed into an active ester will thus be transferable to a specific position on the surface of a protein or peptide comprising a structure according to the invention. Peptides, proteins, PNAs, carbohydrate derivatives, drugs, inhibitors are examples of such transferable substances. Several lysine residues of a protein or peptide with a structure according to the invention can be acylated, one after the other, in a controlled way so that complex sites, or epitopes, can be designed that are formed from several different ligands, and the concept can also be exploited in a combinatorial approach to form a large number of different binding sites. The binding of a protein or peptide with a structure according to the invention to a surface by a covalent bond can be accomplished in a controlled way using the same chemical reaction that is used to bind the different ligands.

The bond forming reaction according to the invention can be performed in an aqueous solution by adding the active ester to a solution of a protein or peptide with a structure according to the invention, preferably at pH 6 and room temperature. After the reaction is complete, any excess ester and the leaving group are washed away, and a new ester can be added. The formation of e.g. a complex protein receptor or a binding site can thus be accomplished using very simple step-wise chemistry, and it does not depend on the use of expensive or hazardous coupling agents because the reactivity and site selectivity is encoded into the protein or peptide with a structure according to the invention. The site selective incorporation of substituents requires that optimized concentrations of active esters are used in the reaction. If a peptide is subjected to prolonged treatment with a large excess of ester then the selectivity will decrease, but if the peptide is subjected to an optimized concentration of ester then the intramolecular competition will ensure that the optimum yield of selectively functionalized peptide is obtained. The optimum concentrations and reaction times differs between different lysine side chains because the different geometrical relationship between His and Lys residues gives rise to acyl transfer reactions that are not equal. The experimental conditions described for the present invention have been standardized for comparison between different sites and can be further optimized. The introduced substituents are also known to influence the incorporation at a neighboring site because of its size and other molecular properties, such as for example charge and polarity. When the protein that has been bound to a surface by a covalent bond is a homodimer then only one of the peptides is covalently linked, and the other peptide can be replaced to form a heterodimer. The functionalized protein is readily removed from the surface and replaced with a second one in a very short period of time (a few seconds or minutes), so that a new reaction can be performed.

Examples of targets are proteins and other biomolecules that are extracted from, e.g., cell lysates. Combinatorially composed surfaces can then be used in the search of the "unknown proteins" that are not readily predictable form the genes in the cell, perhaps because they have been posttranslationally modified, so that their function is not predictable from the DNA sequence.

An added value is the capability of constructing tailor-made affinity columns form purification and isolation. The receptor or binding site that were used for example to find a specific protein from a cell lysate can be constructed in large enough quantities to be used for its purification and isolation.

One object of the present invention is to provide an improved method of performing an acyl transfer type reaction using an imidazole based catalyst. There is therefore provided an improved method of performing a chemical reaction involving an acyl transfer mechanism in the presence of an imidazole-based catalyst which can form a transition complex with the acyl group.

In a preferred embodiment of the method, the chemical structure element constitutes or is part of a larger structure having a functional group in such a neighboring position that it can be site-specifically functionalized through the acyl transfer via the above intermediary complexes.

In the method of the present invention a chemical structure element with improved capability of catalyzing an acyl transfer reaction is used. There is therefore provided a chemical structure element comprising backbone structure with a pendant imidazole function.

In one embodiment, the structure element is a molecule, such as a peptide or protein, comprising a function in such a neighboring position that it can be site-specifically functionalized through the acyl transfer via the above intermediary complexes.

Another object of present invention is to provide a method of producing by genetic engineering a protein or peptide constituting or comprising a structure element having an imidazole function. It therefore provides a method of producing a protein or peptide which constitutes or comprises an imidazole function-containing structure element as defined above, which method comprises transforming a host organism with a recombinant DNA construct comprising a vector and a DNA sequence encoding said protein or peptide, culturing the host organism to express said protein or peptide, and isolating the latter from the culture.

Still another object of the present invention is to provide a vector comprising a nucleic acid sequence encoding the above protein or peptide. The invention therefore provides a recombinant DNA construct comprising a vector and a DNA sequence encoding a protein or peptide which constitutes or comprises an imidazole function-containing structure element as defined above.

In a preferred embodiment of the vector, the DNA sequence also encodes a specific functional group in a such a neighboring position to the imidazole function that the functional group can be site-specifically functionalized through acyl transfer catalyzed by the imidazole function.

Thus, the present invention is based on the concept of increasing the imidazole type catalytic activity in acyl transfer reactions by providing the imidazole function on a backbone structure with a pendant flanking group (or groups) or chain on one or both sides of the imidazole function, which flanking group or groups can interact with the imidazole-acyl complex formed such that the transition complex is stabilized. The reaction rate for the desired acyl transfer reaction, such as an amidation, trans-esterification, hydrolysis or thiolysis, will be increased considerably thereby. While esters are the currently preferred substrates, e.g. amide and anhydride substrates can also be used.

The term "imidazole function" is to be interpreted broadly, and is meant to encompass any imidazole-based structure that possesses the desired catalytic activity. The imidazole group can consequently be modified in various ways. An advantageous imidazole function for many purposes is based on the amino acid histidine ($\alpha$-amino-4-(or 5)-imidazolepropionic acid). One or both of the available carbon atoms of the imidazole function can, for example, be independently substituted with alkyl or halogen. The imidazole group can also be substituted in 1-position with alkyl. Alkyl has preferably 1 to 6 carbon atoms, especially 1 to 4 carbon atoms, e.g. methyl or ethyl. Halogen includes fluorine, chlorine, bromine and iodine.

The flanking group or groups can comprise a link or chain of, e.g., 1 to 6, preferably 1 to 4 atoms, usually carbon atoms, connected to a terminal functional group or other group capable of the required molecular interaction with the acyl transition complex.

In case the catalytic structure element is a peptide and the imidazolyl function is part of a histidine residue, the flanking chain or chains can be pendant proton donating parts of other amino acids, e.g. selected from lysines, ornithines, arginines and/or further histidines.

The chemical structure element supporting the catalytic imidazolyl function should preferably have some type of rigidity, such as secondary structure, in order to localize the flanking group or groups with respect to the imidazolyl function in an optimal geometric relationship for the desired transition complex-stabilizing interactions to take place. In an advantageous embodiment, the chemical structure element is a so-called designed polypeptide with a stabilized secondary structure, e.g. $\alpha$-helical coiled coils. Designed helical peptides are, for instance, described in J. W. Bryson et al., Science, 270, 935 (1995). The structure element is, however, not limited to a peptide. On the contrary, it can have a variety of compositions readily apparent to the skilled person in the light of the present invention, and can thus be included in or be part of other types of structures, such as a carbohydrate, a natural or synthetic polymer, etc. The size of the chemical structure is not either limiting, and it can, e.g., be a peptide of as few as, say, five amino acids. As to the required geometric relationship between imidazole function and flanking group or groups, a functional arrangement can readily be designed for each particular situation by the skilled person after having read the present description.

Depending on the functional moiety of the complex-stabilizing flanking chain or chains, the transition complex can react with such a flanking chain in an intramolecular reaction. Such an intramolecular reaction can be used for selectively functionalizing peptides, proteins and other molecules.

It is readily understood that designed polypeptides embodying the present invention, such as those mentioned above, can be produced by recombinant DNA technology (genetic engineering). Such techniques are well known and to the skilled person and will not be described herein. (It can, for example, be referred to EP-B1-282 042 which discloses the preparation by recombinant technology of fusion proteins which contain neighboring His-residues.)

The above described selectivity of the reaction center can be used to introduce new functionality in e.g. folded polypeptides. In an intramolecular reaction, the stabilizing flanking group(s) need, of course, not be the one to be functionalized through the acyl transfer but can be another functional group in an appropriate position.

An important aspect of site-selective functionalization is the introduction of carbohydrates site-selectively into proteins and peptides. This is accomplished by modifying the carbohydrate in question to contain an ester function. Carbohydrates play an important role in the recognition in immunological, inflammatory and other processes. They can enhance the immunogenicity of proteins and peptides. They also protect proteins from proteolytic degradation and affect protein folding. Site-selective introduction of carbohydrates can therefore be used for antibody production and vaccine development and the systematic study of the role of carbohydrates. It can also be used to protect drugs from degradation.

The reaction can also be used to introduce residues that will not survive under the reaction conditions of peptide synthesis or that will not be reactive enough due to steric hindrance. Novel branched polypeptide structures are also possible if amino acid residues or peptides can be introduced. Since the histidine is regenerated, it can also be designed to participate in the active site of an engineered catalyst.

The peptide to be functionalized is dissolved in a buffer solution at pH 5.85 and the first ester is added at a concentration that has been estimated from the comparison between the pseudo first-order rate constant of the peptide catalyzed reaction (calculated from the second-order rate constant and the peptide concentration) and the background reaction. For example, if the second-order rate constant is 0.039 M–1 s–1, then at a peptide concentration of 1 mM, the pseudo first-order rate constant is $3.9 \times 10^{-5}$ s–1, a factor of 3.9 larger than that of the background reaction. The fraction of substrate that reacts with the peptide is then at the beginning of the reaction 3.9/(1+3.9)=0.8 and the excess ester shall be 25%. However, as the reaction proceeds the concentration of unfunctionalized peptide decreases and thus the effective pseudo first-order rate constant. Therefore an excess of 60% is used in this case, the magnitude of the excess being estimated from the theoretical calculation in combination with experience from experimental measurements. The reactivities of the ester substrates are known from separate kinetic experiments, and when all the substrate has been consumed a second ester is added which will predominantly go into the second most reactive site, using the same procedure as described above. When that has been consumed a third substrate is added, and so on until all the lysine residues to be functionalized have been saturated. At this stage the peptide is purified by HPLC as described elsewhere. For some positions excesses of a factor of ten or so of ester substrate may be necessary to obtain the optimum incorporation, because the partitioning between hydrolysis and incorporation favors hydrolysis. This fact does not in any way decrease the site selectivity of the incorporation. On the contrary, it increases it.

Alternatively, if a substrate ester is insoluble in water, it can be introduced into the sequence during the solid phase peptide synthesis using orthogonal protection group strategies. For example, an allyl protection group can be used for a lysine residue which can be selectively removed before the peptide is cleaved from the resin, and the lysine can be reacted with the hydrophobic substituent using standard carbodiimide coupling reagents.

Alternatively, some substituents may require HPLC purification at an intermediate stage of the functionalization, if the chromatographic properties of multifunctionalized proteins do not differ appreciably.

Alternatively, some substrates may function better at different pH values of the buffer. 2,4-dinitrophenyl esters will, for example be incorporated very efficiently at pH 4–5 due to their inherent high reactivity. This will allow the introduction of several esters simultaneously into the reaction vessel, and the reaction is then controlled by a change of pH. For example, a mixture of three esters is added to a peptide, which is held at pH 4. One ester is a 2,4-dinitrophenyl ester, which reacts readily at pH 4 and is thus incorporated at the most reactive Lys. Then the pH is raised to pH 5 and the N-hydroxisuccinimide ester reacts and is incorporated into the second most reactive Lys site. Finally the pH is raised to 6 and the p-nitrophenyl ester is incorporated at the third most reactive site.

Alternatively, the incorporation is performed at the surface of a solid support, e.g. a gold plate in a Biacore instrument. Then the first reaction is used to form a bond between the active ester attached to the surface using e.g. thiol derivatives that are well known to bind to gold, and the most reactive Lys. Then an ester substrate is introduced into the reaction chamber and reacted to form an amide at the second most reactive site, and so on.

DETAILED DESCRIPTION OF THE INVENTION

Figure 1:
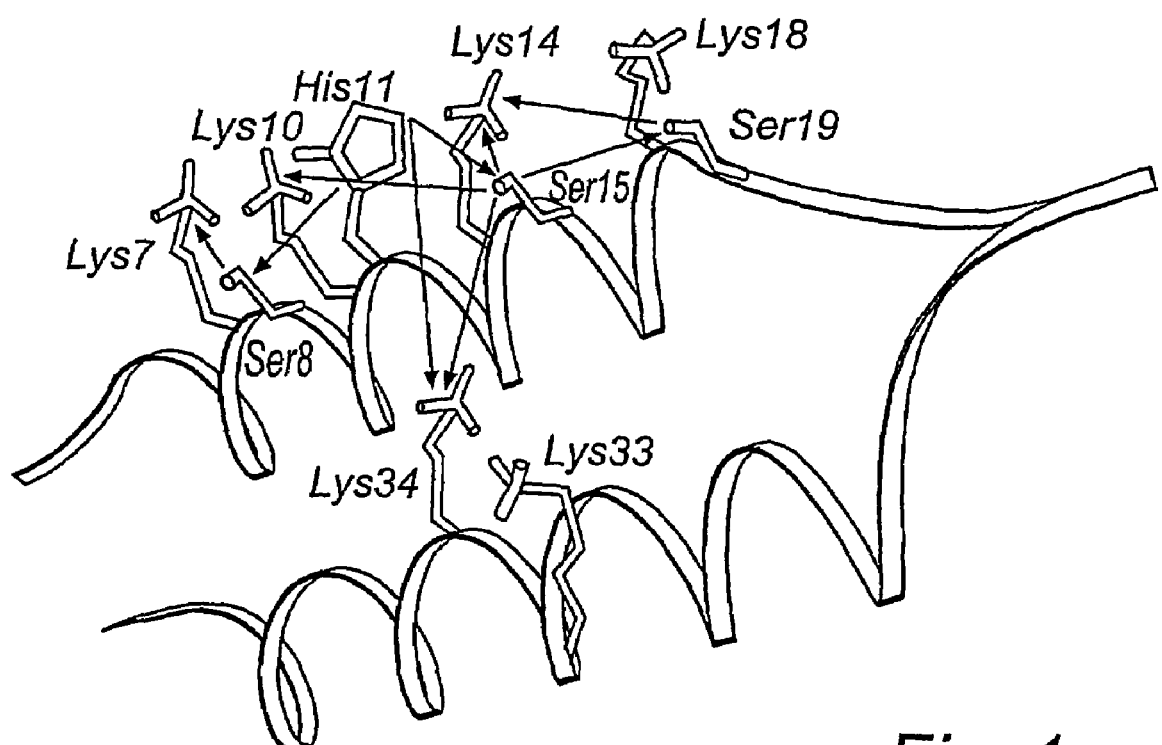
FIG. 1 is a modeled structure of a monomeric hairpin helix-loop-helix motif showing the positions of the residues that form the catalytic network; the sequences are those of the peptides described below; the arrows indicate the acyl migration pathways from His-11 to Lys-7, Lys-10, Lys-14 and to Lys-34.

A model protein, the 84-residue helix-loop-helix homodimer described and characterized in detail elsewhere[6,7], FIG. 1, was redesigned to have Ser residues i–3, i+4 and i+8 relative to a His(i), and with Lys residues in positions that could not be acylated directly by the acylimidazole intermediate on the His side chain. The resulting 42-residue peptides, given in table II below, were synthesized on a PerSeptive Biosystems Pioneer automated peptide synthesizer using a Fmoc-PAL-PEG-PS polymer, standard commercial protocols and Fmoc protection group chemistry, purified using reversed phase HPLC on a semi-preparative Kromasil column using 36–38% isopropanol in 0.1% trifluoroacetic acid and identified using electrospray mass spectrometry (ESMS). The mean residue ellipticities at 222 nm and 300 μM concentration were measured and typical values were −19000 deg cm$^2$dmol$^{-1}$. The geometric relationship between the amino acids is shown in FIG. 1. The proteins at 1 mM concentration in aqueous solution and pH 5.1 was reacted with an excess, typically 40–60%, of mono-p-nitrophenyl fumarate (I). The excess amounts of substrate were needed since background hydrolysis wastes some of the ester, and the excess amount was estimated from the relative magnitudes of the second-order rate constants[8],

TABLE I

Second-order rate constants for self-catalyzed reactions of various peptide with mono-p-nitrophenyl fumarate at pH 5.85 and 298 K.

| Peptide | $K_2/(M^{-1}s^{-1})$ |
|---|---|
| S-I | $3.9 \times 10^{-2}$ |
| S-II | $3.9 \times 10^{-2}$ |
| S-III | $7.1 \times 10^{-2}$ |
| S-IV | $7.5 \times 10^{-2}$ |
| 4-methyl imidazole | $1.7 \times 10^{-2}$ |
| uncat (s$^{-1}$) | $1.0 \times 10^{-5}$ |

TABLE II

The amino acid residues in the positions marked in bold text in the sequence below (SEQ. ID. No. 1) were altered for the peptides as shown below.

```
       1                    11      15         19
Ac-N-A-A-D-Nle-E-A-X-I-K-H-L-A-X-X-Nle-A-X-X 20    23
                                   -G-P-V-D 42             34                   24
NH2-G-A-R-A-F-A-E-F-X-X-A-L-Q-E-A-Nle-Q-A-A
```

| Peptide | Pos 8 | Pos 14 | Pos 15 | Pos 18 | Pos 19 | Pos 33 | Pos 34 |
|---|---|---|---|---|---|---|---|
| S-I (SEQ. ID. No. 2) | A | E | S | A | K | K | Orn |
| S-II (SEQ. ID. No. 3) | S | E | A | A | K | K | Orn |
| S-III (SEQ. ID. No. 4) | A | K | S | A | K | K | Orn |
| S-IIIb (SEQ. ID. No. 5) | A | K | S | A | K | K | A |
| S-IIIc (SEQ. ID. No. 6) | A | K | A | A | K | K | A |
| S-IV (SEQ. ID. No. 7) | S | K | A | A | K | K | Orn |
| S-VIII (SEQ. ID. No. 8) | A | E | S | K | S | K | A |
| S-IX (SEQ. ID. No. 9) | A | E | S | K | A | K | A |
| S-X (SEQ. ID. No. 10) | A | E | A | A | K | K | S |
| S-XII (SEQ. ID. No. 11) | S | E | A | A | K | K | A |

Table 1. The resulting proteins were analyzed by HPLC, using analytical columns, and by ESMS (MW of the monomeric peptide S-I for example is 4333, found 4333, and that of the corresponding monofumarylated peptide is 4431, found 4431), with and without prior tryptic cleavage to identify the site of amidation as described earlier[2]. The fragments expected upon trypsin cleavage are well defined and informative as the peptide is cleaved on the C-terminal side of basic residues, unless the side chain has been modified by fumarylation in which case it is not cleaved at that residue.

The sequences of these peptides are given in the appended sequence listing.

As described above, if His(i) is flanked by Lys (i+4) then Lys (i+4) is exclusively amidated under the reaction conditions used here. If a His is flanked by a lysine residue in a neighboring helix in such a conformation that the Lys has a similar geometric relationship to the His, as has a Lys(i+4) or Lys(i−3) to a His(i), then this Lys will be amidated by the His in a direct acylation reaction. In the sequences S-I (SEQ. ID. No. 2), S-II (SEQ. ID. No. 3), S-III (SEQ. ID. No. 4) and S-IV (SEQ. ID. No. 7) Orn-34 occupies such a position and in the absence of a Lys in position 15 Orn-34 will be preferentially amidated by His-11.

When His-11 was flanked by Ser-15 As in S-I (SEQ. ID. No. 2), FIG. 1, the degree of acylation of Orn-34 was enhanced considerably in comparison with that obtained with the sequence S-II (SEQ. ID. No. 3), where the Ser was in position 8, showing that acylation is mediated by Ser-15. In these peptides no other Lys residues WERE in positions to accept acyl groups by direct transfer from His-11, and no amidations of residues other than Orn-34 were observed. When His-11 was flanked by Lys-14, in the peptide S-IV, FIG. 1, in an i, i+3 configuration, no acylation of Lys-14 was found in agreement with the earlier report that i, i+3 configurations do not lead to amidation[5]. However, when the His-11 Lys-14 pair was supplemented by Ser-15, in the peptide S-III, amidation of Lys-14 was obtained, showing that Ser-15 mediated the transacylation reaction. Ser-15 can be conceived of as playing several roles in catalyzing the amidation of Lys-14. However, the most likely is that it is acylated by the acylimidazole to form an ester intermediate, that is subsequently trapped by Lys-14 in an intramolecular acyltransfer reaction. Alternatively, Ser-15 can simply hydrogen bond to the developing oxyanion in the transition state of the amidation reaction or accept a hydrogen bond from Lys-14 and increase the population of conformers where Lys-14 is in a reactive conformation. However, the low binding energy of hydrogen bonds involving uncharged species in aqueous solution[9] makes both of these alternative explanations less likely. Consequently, if the flanking residue of a His(i) is a serine (i+4) then the acyl group is captured by the hydroxyl group to form an ester, but as the ester is not the thermodynamically most stable species the acyl group migrates further to finally "park" at the side chain of a lysine (i+3 relative to the His, i−1 relative to the Ser) or it is hydrolyzed if no Lys is available for acylation.

Orn-34 is preferentially amidated by His-11 in S-I, S-II, S-III and S-IV so Orn-34 was replaced by Ala in the sequences S-IIIb and S-IIIc. S-IIIb contains Ser-15 whereas in S-IIIc Ser-15 has been replaced by Ala-15. In S-IIIb, Lys-10 and Lys-14 are amidated, whereas in S-IIIc amidation of Lys-10 and Lys-14 is not detected.

In order to probe whether more extended serine pathways could be found, Ser-15 was supplemented by a Ser-19, i.e. i+8 relative to the histidine, while Lys-14 was replaced by a glutamate, to form the peptide S-VIII, FIG. 1. Since Ser-15 can function as an acylating agent for Lys-14, i.e. in an i, i−1 pathway as described above, but probably not in an i, i+3 pathway, acyl migration from Ser-15 to Ser-19 is necessary in order to accomplish amidation via Ser-19. When the protein is reacted with I under the conditions described above, acylation of Lys-10 is observed when Ser-19 is incorporated (S-VIII) but abolished when Ser-19 is replaced by Ala (S-IX). Consequently, acyl groups can migrate from serine to serine in helical segments in an i, i+4 pathway. Acyl groups can therefore migrate long distances over protein surfaces or in protein cavities provided that the appropriate groups are organized in a way to accommodate the structural requirements for intramolecular transesterification.

In the peptide S-XII Ser-8 has been incorporated, as well as Lys-7, and efficient amidation of Lys-7 was observed, demonstration a His(i), Ser(i−3), Lys(i−4) pathway.

The migration of acyl groups over long distances has thus been demonstrated in model proteins using His-Ser, Ser-Ser and Ser-Lys pathways, in addition to the His-Lys pathways reported earlier, but other pathways axe clearly possible. The complexity and significance of this aryl-transfer reaction has only begun to become unraveled as the potential of tyrosines, threonines, cysteines and arginines in providing additional pathways has not been analyzed. The transfer pathways from His to Ser, from Ser to Lys and between other residues also have not been fully mapped. In addition, the determination of which groups can be transferred remains to be demonstrated. The reaction suggests that acyl intermediates in proteolytic cleavage of peptides and esters can escape nucleophiles by fast migration to other sites where the hydrolysis reaction is the most efficient. It also suggests that this reaction can be used to posttranslationally modify proteins and that perhaps phosphoryl groups can be transferred over protein surfaces to the final site of protein phosphorylation.

The rate of transacylation cannot be measured as it is not rate limiting, but the degree of amidation of each available side chain is clearly dependent on the relative magnitude of its rate of acylation suggesting that different side chains can be amidated in a stepwise fashion determined by the relative geometries, distances, pKa values etc of each site. The reactivity of the protein site is controlled by the pKa values of the His residues[10] and by the reactivity of the leaving group[11] but the partitioning of acyl groups between different sites is determined by the structure of the protein. Hydrolysis also competes with intramolecular acyl migration and a fraction of the reactants is clearly lost, although a very small one.

For organic chemists the discovered reaction provides the opportunity to use a simple one-step reaction in aqueous solution to form new proteins with tailor made properties. The introduction of several ligands in a controlled way that recognize and bind known or unknown proteins can prove to be an important one in the upcoming era of proteomics.

REFERENCES

1. Baltzer, L., et al., J. Chem. Soc. Perkin Trans. 2, 1996, 1671–1676.
2. Broo, K., et al., J. Am. Chem. Soc, 1996, 118, 8172–8173.
3. Bruice, T. C. et al., J. Am. Chem. Soc. 1958, 80, 2265–2271.
4. Lundh, A.-C., et al., J. Chem. Soc. Perkin Trans. 2, 1997, 209–212.
5. Broo, K., et al., J, Chem. Soc. Perkin Trans. 2, 1997, 397–398.
6. Olofsson, S., et al., J. Chem. Soc. Perkin Trans. 2, 1995, 2047–2056.
7. Olofsson, S., et al., Folding Des. 1996, 1, 347–356.
8. Andersson, L., et al., J. Org. Chem. 1998, 63, 1366–1367.
9. Structure and mechanism in protein science, Alan Fersht, 1999, W. H. Freeman and Co Ch. 11.
10. Broo, K. S., et al., J. Am. Chem. Soc. 1998, 120, 4063–4068.
11. Nilsson, J. et al. Chem. Eur. J. 2000, 6, 2214–2220.

The invention claimed is:

1. A method for site-selective acyl transfer in or amidation of folded polypeptides and proteins comprising bringing the polypeptide or protein in contact with an acyl group donor, wherein:

said polypeptide or protein comprises a helical secondary structure, said helical secondary structure comprises a histidine in position i flanked by at least one amino group to be amidated in position i+3+4k, wherein k is −1, 0, 1, or in position i−4−4n, wherein n is 0, 1 or 2, said polypeptide or protein further comprises at least one serine, threonine, tyrosine, or cysteine in position i+4+4n or i−3−4n, respectively, wherein n is 0, 1 or 2, and i is the position of an amino acid.

2. The method according to claim 1, wherein said at least one amino group is from a lysine, ornithine or a diaminobutyric acid residue.

* * * * *

UNITED STATES PATENT AND TRADEMARK OFFICE
CERTIFICATE OF CORRECTION

PATENT NO. : 7,230,072 B2  
APPLICATION NO. : 10/258445  
DATED : June 12, 2007  
INVENTOR(S) : Lars Baltzer Page 1 of 1

It is certified that error appears in the above-identified patent and that said Letters Patent is hereby corrected as shown below:

On the Title Page insert item

(30) Foreign Application Priority Data

May 5, 2000 (SE) ......0001698-0

Signed and Sealed this

Twenty-second Day of January, 2008

JON W. DUDAS  
*Director of the United States Patent and Trademark Office*